US012569357B1

(12) United States Patent (10) Patent No.: US 12,569,357 B1

Westbrook et al. (45) Date of Patent: Mar. 10, 2026

(54) HANDLE ADAPTER AND KIT FOR LIMB DIFFERENCES

(71) Applicant: FORM5 PROSTHETICS INC., Westerville, OH (US)

(72) Inventors: Aaron Westbrook, Reynoldsburg, OH (US); Gregory Thune, Westerville, OH (US)

(73) Assignee: FORM5 PROSTHETICS INC., Westerville, OH (US)

( * ) Notice: Subject to any disclaimer, the term of this patent is extended or adjusted under 35 U.S.C. 154(b) by 0 days.

(21) Appl. No.: 19/236,202

(22) Filed: Jun. 12, 2025

(51) Int. Cl.
A61F 2/58 (2006.01)

(52) U.S. Cl.
CPC .............. A61F 2/588 (2013.01); A61F 2/585 (2013.01)

(58) Field of Classification Search
CPC .... A61F 2/54; A61F 2/58; A61F 2/582; A61F 2/585; A61F 2/588; A61F 2/78; A61F 2/80; A61F 2002/543; A61F 2002/546; A61F 2002/5096; A61F 2002/5098; A61F 2002/785; A61F 4/00; B26K 21/125; G05G 1/54
See application file for complete search history.

(56) References Cited

U.S. PATENT DOCUMENTS

| | | | | | |
|---|---|---|---|---|---|
| 35,686 | A | * | 6/1862 | Jewett | A61F 2/80 |
| | | | | | 623/53 |
| 953,821 | A | * | 4/1910 | Dorrance | A61F 2/588 |
| | | | | | 623/65 |
| 2,333,009 | A | * | 10/1943 | Hosmer | A61F 2/54 |
| | | | | | 623/65 |
| 2,905,492 | A | * | 9/1959 | Alexander | F16C 11/0609 |
| | | | | | 403/130 |

(Continued)

FOREIGN PATENT DOCUMENTS

| | | | | | |
|---|---|---|---|---|---|
| GB | 2278281 | A | * | 11/1994 | A61F 2/72 |
| WO | WO-2016020317 | A1 | * | 2/2016 | A61F 2/74 |
| WO | WO-2021021754 | A1 | * | 2/2021 | B25B 5/06 |

OTHER PUBLICATIONS

Unyq. UNYQ raises $1 Million. 3dprint.com (Year: 2016).*

(Continued)

*Primary Examiner* — Christie Bahena

(74) *Attorney, Agent, or Firm* — McNees Wallace & Nurick LLC

(57) ABSTRACT

A limb differential handle adapter is disclosed including a split coupling mount, a rotational joint, and a differential limb socket. The split coupling mount is configured to removably attach to a handle. The split coupling mount has an internal surface configured to contact the handle and an external surface. The rotational joint is configured to removably attach to and extend from the external surface of the split coupling mount. The rotational joint includes a socket, (Continued)

an interface disposed in the socket, and a shaft extending from the interface. The differential limb socket is configured to receive a differential limb and includes at least one replaceable modular insert proportioned to accommodate the differential limb. The differential limb socket is removably coupled to the rotation joint. A limb differential handle adapter kit is disclosed further including interchangeable components for the at least one replaceable modular insert and a plurality of shims.

22 Claims, 9 Drawing Sheets

(56) References Cited

U.S. PATENT DOCUMENTS

| | | | |
|---|---|---|---|
| 9,956,093 B1 * | 5/2018 | Harris | A61F 2/76 |
| 2005/0234564 A1 * | 10/2005 | Fink | A61F 2/583 |
| | | | 623/64 |
| 2015/0065310 A1 * | 3/2015 | Quinn | A63B 21/0421 |
| | | | 482/62 |
| 2023/0338172 A1 * | 10/2023 | Wellman | A61F 2/7812 |
| 2024/0180722 A1 | 6/2024 | Westbrook et al. | |

OTHER PUBLICATIONS

Universal Design. Pro Cycling Hand Prosthesis. (Year: 2014).*

Form 5. Youtube. The Columbus Foundation. (Year: 2023).*

Translation of WO2016020317A1 (Year: 2016).*

Strider + Ram Mounts, https://www.striderbikes.com/adaptive-strider-program; bears date of Oct. 21, 2022—downloaded Jun. 17, 2025.

Fillauer TRS, https://fillauer.com/bicycling-specific-devices/; undated—weblink available at least as early as Apr. 2025. downloaded Jun. 17, 2025.

Limbo Foundation—Helpful Adaptations, https://limbbofoundation.co.uk/helpful-adaptations/; bears date of Feb. 19, 2024—downloaded Jul. 7, 2025.

Amber Henson, Riding a Bicycle When You Have an Upper Limb Difference, https://www.armdynamics.com/upper-limb-library/riding-a-bicycle-when-you-have-an-upper-limb-difference; bears date of Nov. 1, 2022—downloaded Jul. 7, 2025.

Koala Prosthetics, Say Hello to the ALX, https://www.yourkoalaa.com/sarahalx; undated—weblink available at least as early as Apr. 2025—downloaded Jun. 17, 2025.

Strider, Adaptive Strider program—Custom Strider Bikes for toddlers, https://www.striderbikes.com/; undated—weblink available at least as early as Apr. 2025, downloaded Jul. 7, 2025.

* cited by examiner

10

300

200

100

100

212

300

320

HANDLE ADAPTER AND KIT FOR LIMB DIFFERENCES

FIELD OF THE INVENTION

This application is directed to articles and kits for facilitating persons having limb differences to operate vehicles, conveyances, equipment, machinery, and apparatuses that are typically used in a two-handed manner. More specifically, this application is directed to handle adapters and handle adapter kits for which are adaptable and modular to accommodate the requirements of the particular users having limb differences.

BACKGROUND OF THE INVENTION

Many vehicles and equipment are designed for use primarily with two hands and are, in fact, quite difficult to operate with a single hand, such as bicycles, motorcycles, mopeds, ATVs, jet skis, snowmobiles, strollers, carriages, hand trucks, and carts. Operating vehicles and equipment designed for use with two hands is often quite difficult, or at least inconvenient, for persons having a differential limb, particularly with regard to maintaining balance and steering, and some degree of safety.

Cycling, in one example, remains inaccessible for many individuals with upper limb differences due to discomfort, instability, and the lack of functional adaptive solutions. Existing devices intended to address these challenges are often generic, ill-fitting, or fail to provide the security and control needed for a confident and safe riding experience. As a result, individuals with limb differentials are frequently excluded from the joy and freedom that cycling offers.

Accordingly, it would be desirable to have a solution to the challenges for persons with limb differentials to operate two-handed vehicles or equipment without the disadvantages of existing devices.

BRIEF DESCRIPTION OF THE INVENTION

In one exemplary embodiment, a limb differential handle adapter includes a split coupling mount, a rotational joint, and a differential limb socket. The split coupling mount is configured to removably attach to a handle. The split coupling mount has an internal surface configured to contact the handle and an external surface. The rotational joint is configured to removably attach to and extend from the external surface of the split coupling mount. The rotational joint includes a socket, an interface disposed in the socket, and a shaft extending from the interface. The differential limb socket is configured to receive a differential limb and includes at least one replaceable modular insert proportioned to accommodate the differential limb. The differential limb socket is removably coupled to the rotation joint.

In another exemplary embodiment, a limb differential handle adapter kit includes a limb differential handle adapter. The limb differential handle adapter includes a split coupling mount, a rotational ball-and-socket joint, and a differential limb socket. The split coupling mount is configured to removably attach to a handle. The split coupling mount has an internal surface configured to contact the handle and an external surface. The rotational ball-and-socket joint is configured to removably attach to and extend from the external surface of the split coupling mount. The rotational joint includes a seat portion and a cap portion cooperating to define a socket, a ball interface disposed in the socket, and a shaft extending from the ball interface. The differential limb socket is configured to receive a differential limb and includes at least one replaceable modular insert proportioned to accommodate the differential limb. The at least one replaceable modular insert includes a plurality of ventilation features selected from the group consisting of ventilation apertures, ventilation channels, and combinations thereof. The limb differential handle adapter is free of locking mechanisms restricting disengagement of the differential limb from the differential limb socket. The differential limb socket is attached to the shaft of the rotational joint. The kit further includes a plurality of interchangeable components for the at least one replaceable modular insert to adjust for length, diameter, and shape of the differential limb. The kit further includes a plurality of shims for disposal between the seat portion and the cap portion of the rotational ball-and-socket joint such friction of the rotational joint is adjustable by incorporation of one or more of the plurality of the shims in the rotational ball-and-socket joint. The differential limb socket is attached to the rotational joint via a quick-release connector that is disengageable without use of tools and with a single hand.

Further aspects of the subject matter of the present disclosure are provided by the following clauses:

A limb differential handle adapter includes a split coupling mount configured to removably attach to a handle, the split coupling mount having an internal surface configured to contact the handle and an external surface, a rotational joint configured to removably attach to and extend from the external surface of the split coupling mount, the rotational joint including a socket, an interface disposed in the socket, and a shaft extending from the interface, and a differential limb socket configured to receive a differential limb and including at least one replaceable modular insert proportioned to accommodate the differential limb, the differential limb socket being removably coupled to the rotation joint.

The limb differential handle adapter of the preceding clause, wherein the limb differential handle adapter is free of locking mechanisms restricting disengagement of the differential limb from the differential limb socket.

The limb differential handle adapter of any preceding clause, wherein the limb differential handle adapter is free of locking mechanisms restricting disengagement of the differential limb from the differential limb socket.

The limb differential handle adapter of any preceding clause, wherein the at least one replaceable modular insert includes a plurality of interchangeable components selected from a kit combinable to adjust for length, diameter, and shape of the differential limb.

The limb differential handle adapter of the preceding clause, wherein the plurality of interchangeable components includes padding formed from a material selected from the group consisting of a viscoelastic foam, an open-cell foam, a closed-cell foam, and combinations thereof.

The limb differential handle adapter of any preceding clause, wherein the differential limb socket includes a plurality of ventilation features selected from the group consisting of ventilation apertures, ventilation channels, and combinations thereof.

The limb differential handle adapter of any preceding clause, wherein the differential limb socket includes a moisture wicking layer.

The limb differential handle adapter of any preceding clause, wherein the differential limb socket includes two socket covers which cooperate to form an exterior surface of the differential limb socket, each of the two socket covers being identical to one another.

The limb differential handle adapter of any preceding clause, wherein the rotational joint is selected from the group consisting of a ball-and-socket joint, a condyloid joint, a saddle joint, a hinge joint, a pivot joint, a plane joint, a compound joint, and combinations thereof.

The limb differential handle adapter of any preceding clause, wherein the differential limb socket is attached to the shaft of the rotational joint.

The limb differential handle adapter of any preceding clause, wherein the differential limb socket is attached to the socket of the rotational joint.

The limb differential handle adapter of any preceding clause, wherein the rotational joint includes an adjustable rotational resistance.

The limb differential handle adapter of the preceding clause, wherein the rotational joint includes a seat portion and a cap portion, and the adjustable rotational resistance is adjustable by insertion of at least one shim between the seat portion and the cap portion such that the at least one shim changes friction of the rotational joint.

The limb differential handle adapter of any preceding clause, wherein the rotational joint includes a seat portion and a cap portion, the cap portion is angled so as to limit rotation of the differential limb socket to a predetermined range of orientations, and the cap portion is attachable to the seat portion in a predetermined number of positions such that the predetermined range of orientations is adjustable rotationally relative to the seat portion.

The limb differential handle adapter of any preceding clause, wherein the rotational joint includes a seat portion and a cap portion, the cap portion being selected from a kit having different cap angles and predetermined ranges of orientations.

The limb differential handle adapter of any preceding clause, wherein the differential limb socket is attached to the rotational joint via a quick-release connector that is disengageable without use of tools and with a single hand.

The limb differential handle adapter of any preceding clause, wherein the handle is a handlebar.

The limb differential handle adapter of the preceding clause, wherein the handlebar is a bicycle handlebar.

The limb differential handle adapter of any preceding clause, wherein the handlebar is a motorcycle handlebar, a moped handlebar, an ATV handlebar, a jet ski handlebar, or a snowmobile handlebar.

The limb differential handle adapter of any preceding clause, wherein the handle is a stroller, carriage, cart or hand truck handle.

A limb differential handle adapter kit includes a limb differential handle adapter, including a split coupling mount configured to removably attach to a handle, the split coupling mount having an internal surface configured to contact the handle and an external surface, a rotational ball-and-socket joint configured to removably attach to and extend from the external surface of the split coupling mount, the rotational joint including a seat portion and a cap portion cooperating to define a socket, a ball interface disposed in the socket, and a shaft extending from the ball interface, and a differential limb socket configured to receive a differential limb and including at least one replaceable modular insert proportioned to accommodate the differential limb, the at least one replaceable modular insert including a plurality of ventilation features selected from the group consisting of ventilation apertures, ventilation channels, and combinations thereof, wherein the limb differential handle adapter is free of locking mechanisms restricting disengagement of the differential limb from the differential limb socket, the differential limb socket is attached to the shaft of the rotational joint, the kit further includes a plurality of interchangeable components for the at least one replaceable modular insert to adjust for length, diameter, and shape of the differential limb, the kit further includes a plurality of shims for disposal between the seat portion and the cap portion of the rotational ball-and-socket joint such friction of the rotational joint is adjustable by incorporation of one or more of the plurality of the shims in the rotational ball-and-socket joint, and the differential limb socket is attached to the rotational joint via a quick-release connector that is disengageable without use of tools and with a single hand.

The limb differential handle adapter kit of the preceding clause, wherein the handle is a bicycle handlebar.

BRIEF DESCRIPTION OF THE DRAWINGS

Wherever possible, the same reference numbers will be used throughout the drawings to represent the same parts.

DETAILED DESCRIPTION OF THE INVENTION

Figure 1:
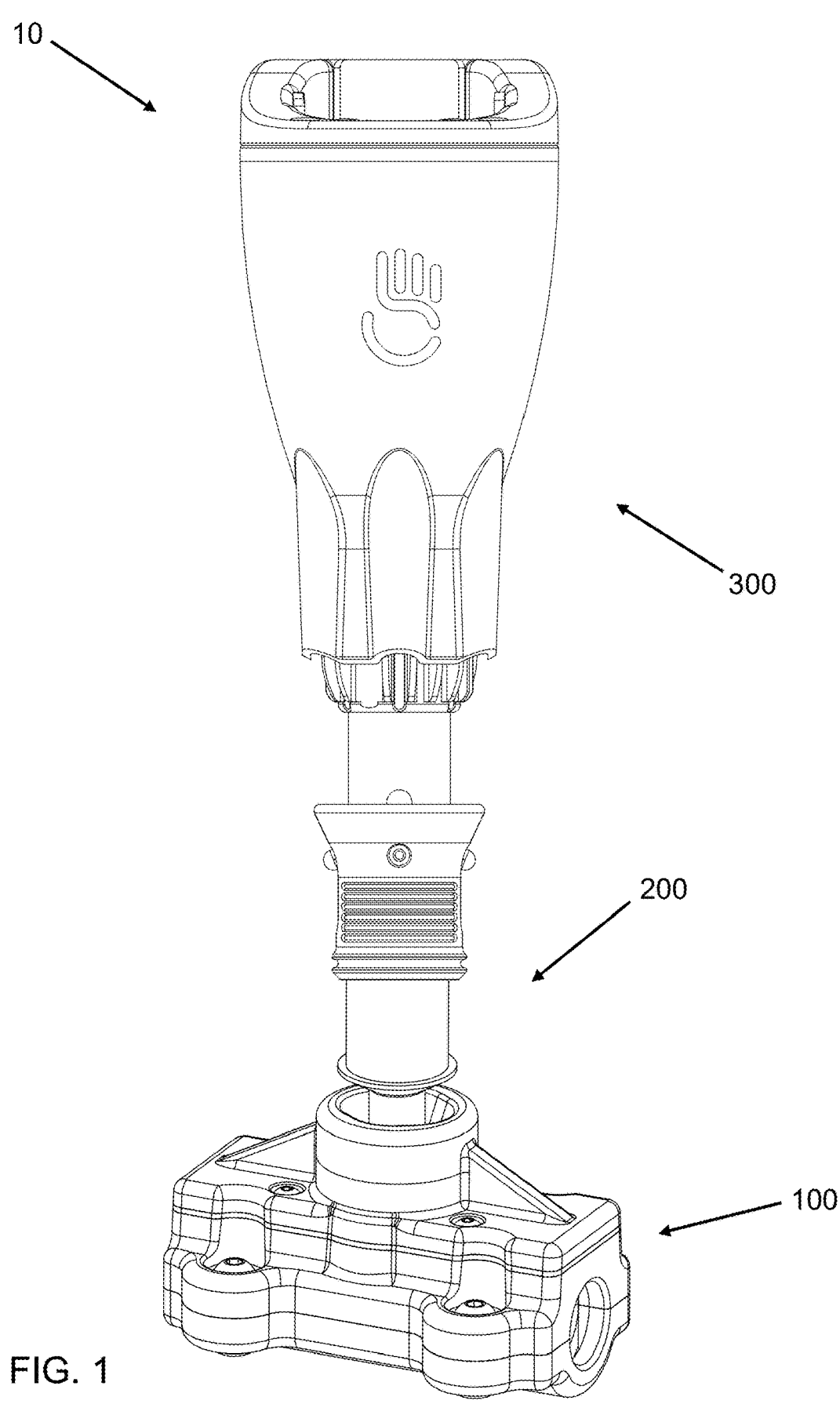
FIG. 1 is a perspective view of an assembled limb differential handle adapter, according to an embodiment of the present disclosure.
Figure 2:
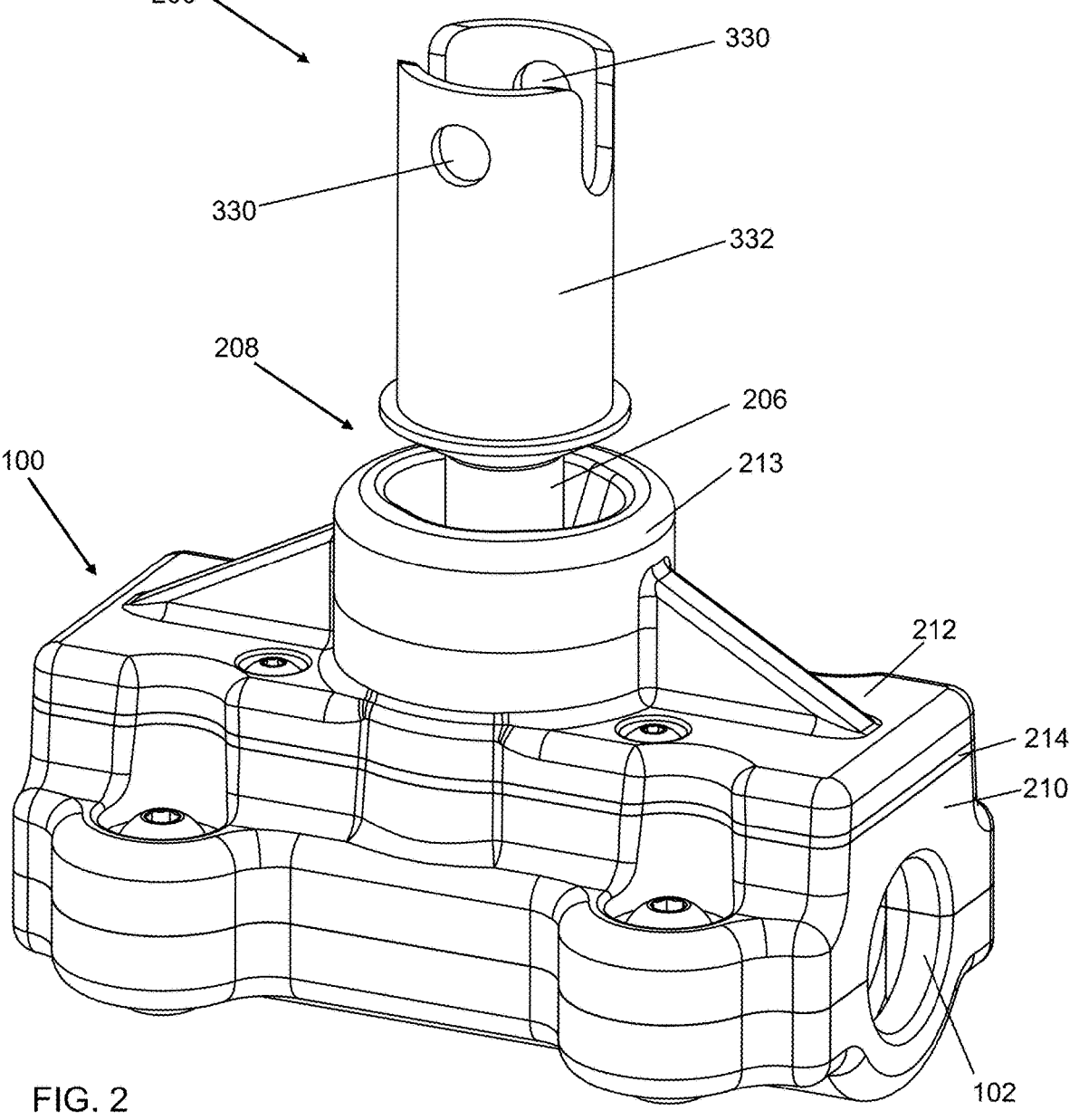
FIG. 2 is a perspective view of the split coupling mount and the rotation joint of the limb differential handle adapter of FIG. 1, according to an embodiment of the present disclosure.
Figure 3:
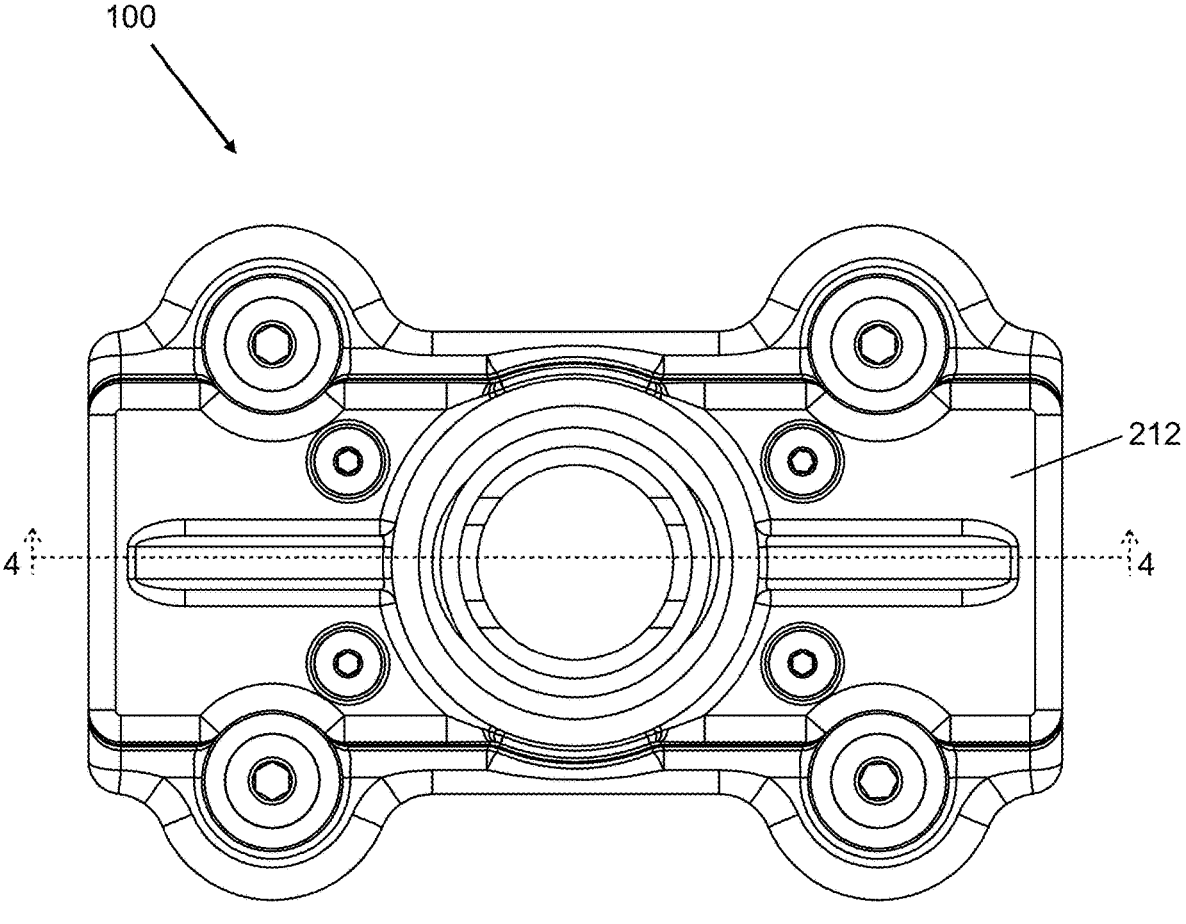
FIG. 3 is a plan view of the split coupling mount and the rotation joint of FIG. 2, according to an embodiment of the present disclosure.
Figure 4:
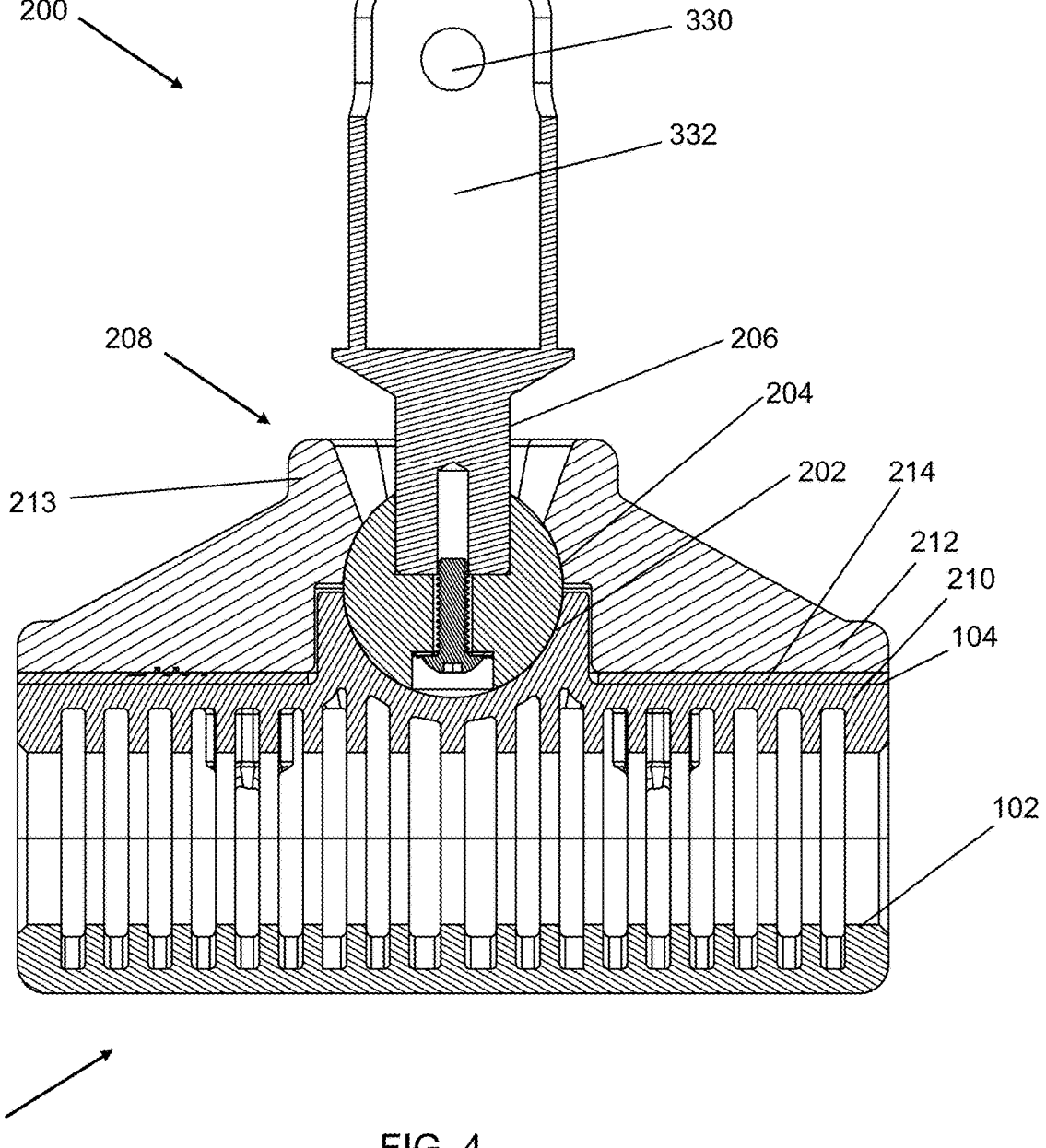
FIG. 4 is cross-sectional view of the split coupling mount and the rotation joint of the limb differential handle adapter of FIG. 3 taken along line 4-4, according to an embodiment of the present disclosure.
Figure 5:
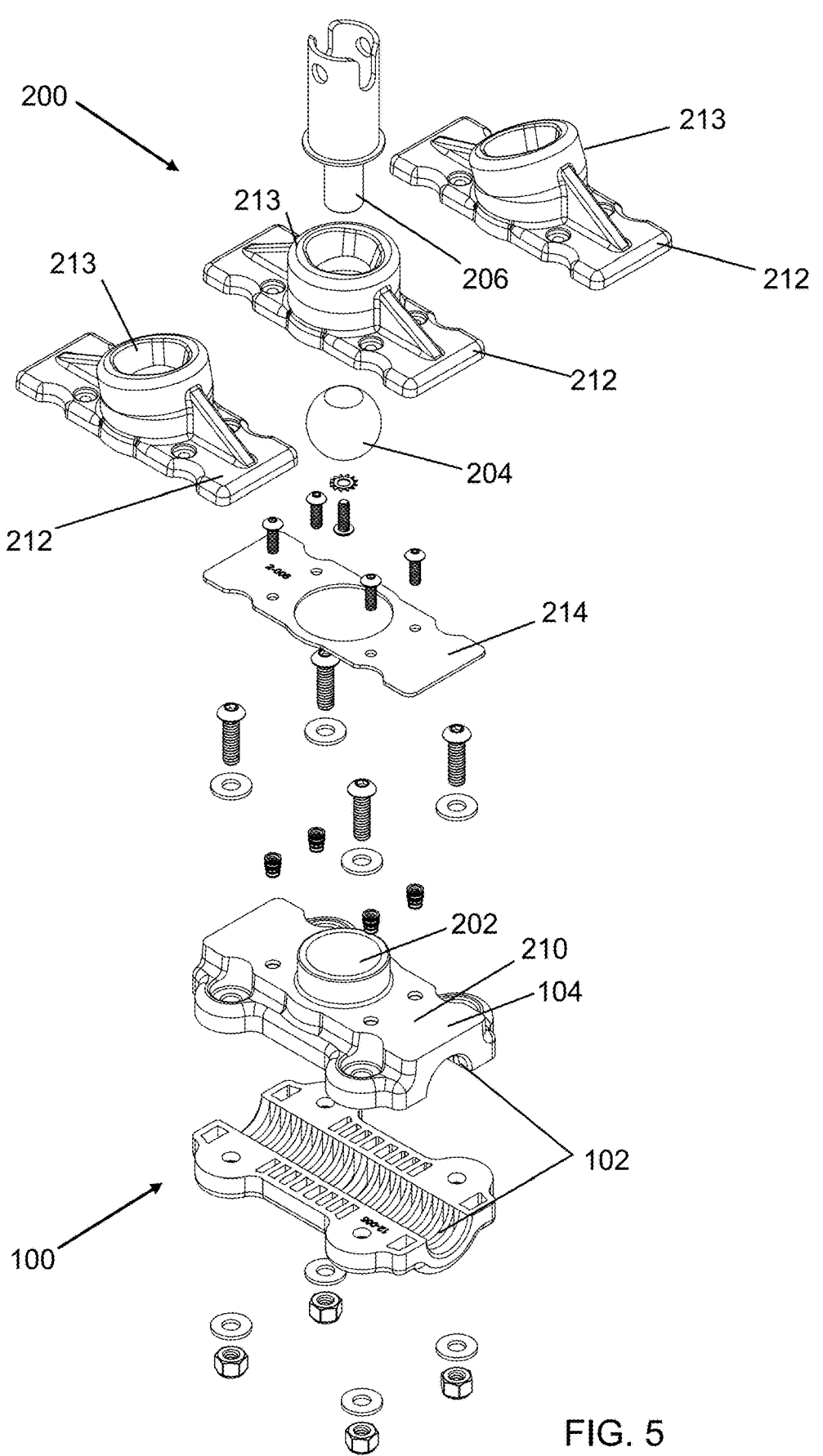
FIG. 5 is an exploded view of the split coupling mount and the rotation joint of the limb differential handle adapter of FIG. 2, according to an embodiment of the present disclosure.

The present limb differential handle adapters and kits, in comparison to adapters and kits lacking one or more of the features described herein, may increase the safety, comfort, case of use, and enjoyment of users having a differential limb in operating vehicles and equipment with handles.

As used herein, "about" indicates a variance of up to 10% of the value so modified, and specifically includes the absolute value as well, such that "about 2" discloses both a range from 1.8 to 2.2 as well as 2.

Referring to FIGS. 1-9, in one embodiment, a limb differential handle adapter 10 includes a split coupling mount 100, a rotational joint 200, and a differential limb socket 300. The split coupling mount 100 is configured to removably attach to a handle 20. The split coupling mount 100 has an internal surface 102 configured to contact the handle 20 and an external surface 104. The rotational joint 200 is configured to removably attach to and extend from the external surface 104 of the split coupling mount 100. The rotational joint 200 includes a socket 202, an interface 204 disposed in the socket 202, and a shaft 206 extending from the interface. The differential limb socket 300 is configured to receive a differential limb and includes at least one replaceable modular insert 302 proportioned to accommodate the differential limb. The differential limb socket 300 is removably coupled to the rotational joint 200. The limb differential handle adapter 10 may be free of locking mechanisms restricting disengagement of the differential limb from the differential limb socket 300. The internal surface 102 of the split coupling mount 100 may include an interface material disposed thereon, such as, but not limited to, a double-sided adhesive tape, an elastic cushion, or combinations thereof, to aid in the clamping compression and tolerance compliance between the split coupling mount 100 and handles 20 of differing diameters.

Referring to FIGS. 2-5, the rotational joint 200 may be any suitable joint, including, but not limited to, a ball-and-socket joint 208, a condyloid joint, a saddle joint, a hinge joint, a pivot joint, a plane joint, a compound joint, or combinations thereof. The differential limb socket 300 may be attached to the shaft 206 of the rotational joint 200 or the socket 202 of the rotational joint 200.

The rotational joint 200 may include an adjustable rotational resistance. In one embodiment, the rotational joint 200 includes a seat portion 210 and a cap portion 212, and the adjustable rotational resistance is adjustable by insertion of at least one shim 214 between the seat portion 210 and the cap portion 212 such that the at least one shim 214 changes the compression on the interface 204, such as, but not limited to, a ball interface 204, thus increasing or decreasing the friction of the rotational joint 200. The at least one shim 214 may be selected from a kit including a plurality of shims 214, which kit may include multiple shims 214 having the same shim thickness, a variety of shim thicknesses, or combinations thereof, such that the adjustable rotational resistance may be adjusted by stacking multiple shims 214 to increase the shim thickness or by selecting an individual shim of a greater or lesser thickness, or combinations thereof. The kit may further include shims 214 having different coatings affecting the adjustable rotational resistance. This kit may include any number of the foregoing options, in any combination, so as to maximize the customizability of the adjustable rotational resistance.

In one embodiment, the rotational joint 200 includes the seat portion 210 and the cap portion 212 in which the cap portion 212 includes a collar 213 that may be angled so as to limit rotation of the differential limb socket 300 to a predetermined range of orientations. The cap portion 212 is attachable to the seat portion 210 in a predetermined number of positions such that the predetermined range of orientations is adjustable rotationally relative to the seat portion 210, and in the context of a handlebar, can be independently used for either a right or a left side. The predetermined range of positions may include a first position and a second position rotated 180° from the first position, or a first position, a second position, and a third position, rotated 120° from one another, or a first position, a second position, a third position, and a fourth position, rotated 90° from one another, or any number of additional positions. A kit may include a plurality of cap portions 212 having different cap angles relative to the seat portion 210, different predetermined ranges of orientations, or combinations thereof. The predetermined range of orientations may be set by shape of the cap portion 212 such that rotation and translation of the differential limb socket 300 is physically restricted. The use of different cap portions 212 may define a maximum level of freedom in the range of motion of a user of the adapter 10 to account for the configuration or sweep of the handlebars to which the adapter is attached and/or greater or lesser skill of the user. This may include both the level of experience of the user in using the adapter 10, as well as the level of experience in the activity in which the user is engaging. This may limit, for example, a tendency for a younger rider to oversteer while a different cap 212 with a flat collar that gives a wider range of motion might be used by a more experienced rider desiring more freedom of control.

Figure 6:
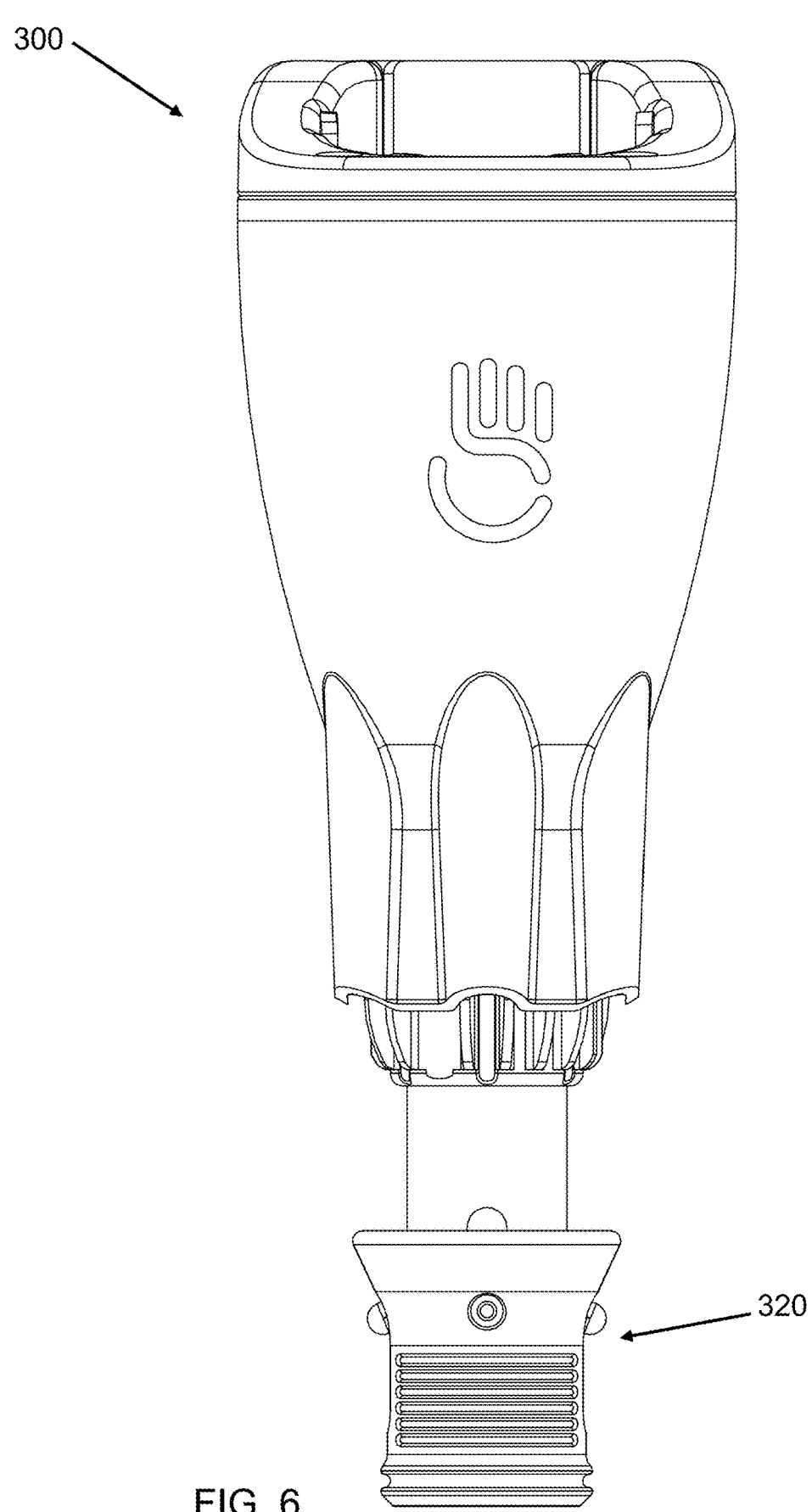
FIG. 6 is an elevation view of the split coupling mount and the rotation joint of the limb differential handle adapter of FIG. 1, according to an embodiment of the present disclosure.
Figure 7:
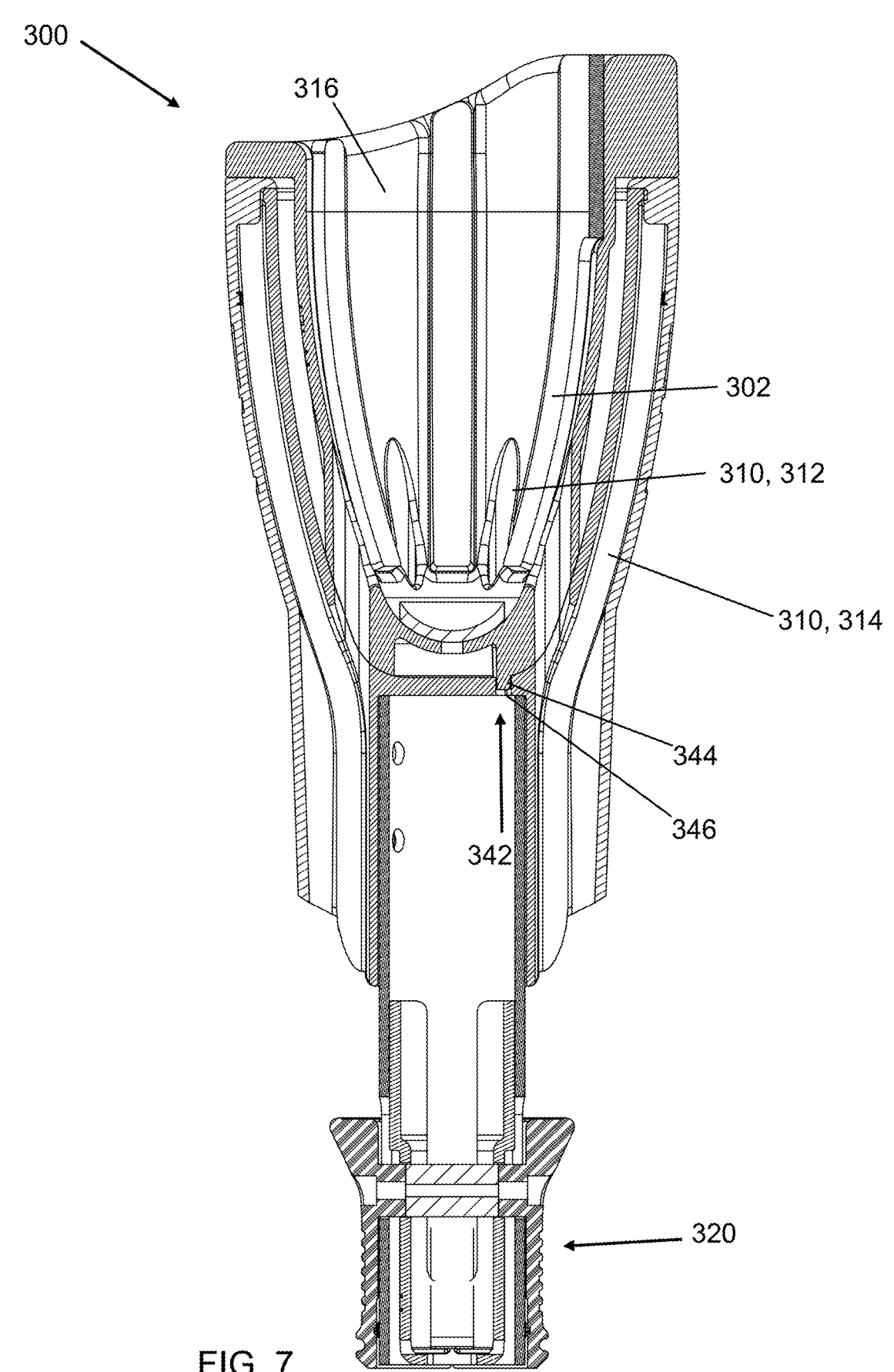
FIG. 7 is a cross-sectional view of the differential limb socket of FIG. 6, according to an embodiment of the present disclosure.
Figure 8:
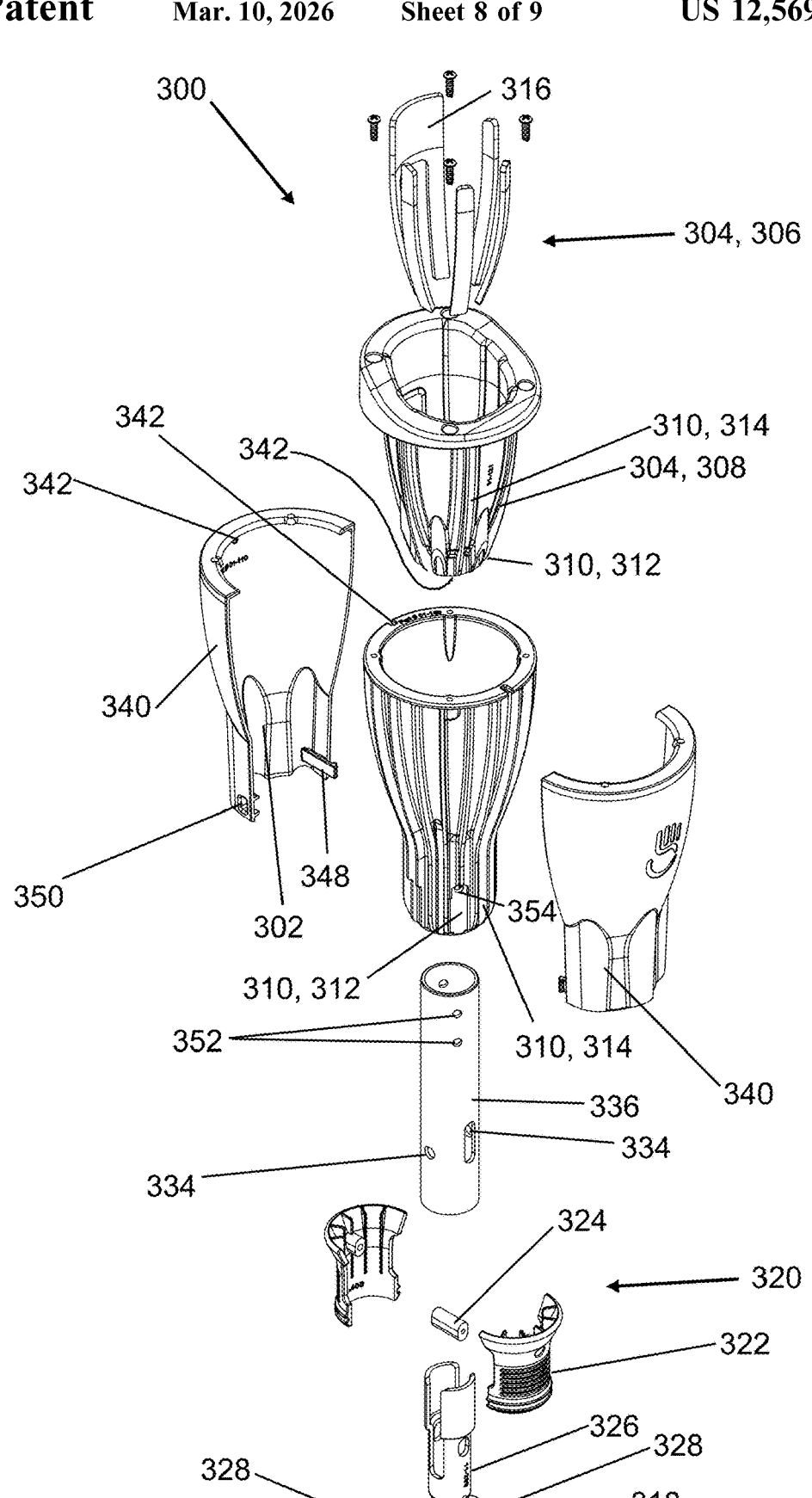
FIG. 8 is an exploded view of the differential limb socket of FIG. 6, according to an embodiment of the present disclosure.

Referring to FIGS. 6-8, the differential limb socket 300 may include a releasable connector 320 for removably coupling with the rotational joint 200. In one embodiment, the releasable connector 320 is a quick-release connector. Exemplary embodiments may advantageously employ a quick-release connector such that the socket 300 is disengageable from the joint 200 with a single hand and without the use of tools. As illustrated, the releasable connector 320 is a telescope clip that locks into place using a v-clip 318, but may move axially to release the connection when the v-clip 318 is manually compressed by the user.

Referring to FIG. 8, in one embodiment, the releasable connector 320 includes a slide button 322 attached to a crossmember 324 which is contained in a release slide 326. To disengage the receptacle 300 from the split coupling mount 100, a user pulls up on the slide button 322, which causes the release slide 326 to slide over the V-clip 318 and in the process compress the v-clip 318 so that button hubs 328 on the v-clip 318 disengage from the stem tube holes 330 in a stem tube 332 thus disengaging the receptacle 300 from the split coupling mount 100. To attach the receptacle 300 to the split coupling mount 100, the user lines up the stem shaft holes 334 on the stem shaft 336 and the stem tube holes 330 on the stem tube 332. The slide button 322 is slid down, forcing the release slide 236 to uncompress the v-clip 318 and allow the button hubs 328 to engage with the stem tube holes 330, attaching the receptacle 300 to the split coupling mount 100.

The differential limb socket 300 may include at least one replaceable modular insert 302 that may include any suitable number of interchangeable components, or cups, 304 from a kit to adjust for length, diameter, and shape of the differential limb. This may include, for example, cups adapted to accommodate low, mid, and upper forearm differentials and diameters to accommodate small, medium and large for, example, typical child, female and male physiology and/or an individual's physiological growth. In one embodiment, the stem shaft 336 includes a plurality of stem shaft holes 352 arranged for the adjustment of the length of the differential limb socket 300, for example, to accommodate growth of a user over time. The plurality of stem shaft holes 352 align with a stem shaft attachment hole 354 to set the length of the differential limb socket 300.

The differential limb socket 300 may include at least one socket cover 340. The socket cover 340 may include a clocking feature 342 for fixing orientation of the socket cover 340 relative the differential limb socket 300. The clocking feature 342 may include, but is not limited to, a clocking projection 344 that aligns with a clocking receptacle 346 disposed in the differential limb socket 300 or in one or more of the at least one replaceable modular insert 302. The at least one replaceable modular insert 302 the interchangeable components, or cups, 304, the padding 306, and the spacers 308 may further including clocking features 342 between and amongst them and the differential limb sock 300 in general. The inclusion of clocking features 342 may promote accurate and speedy assembly.

In one embodiment, the differential limb socket 300 includes two socket covers 340 which cooperate to form an exterior surface of the differential limb socket 300. In a further embodiment, each of the two socket covers 340 is identical to the other such that a single type of part may form both halves of the cumulative socket cover 340. To this end, each of the two socket covers 340 may include a snap feature 348 and a snap receptacle 350 positioned such that when one of the two socket covers 340 is rotated 180° relative to the others, the snap feature 348 engages with the snap receptacle 350 of the other and visa versa.

The plurality of interchangeable components 304 may include padding 306, spacers 308, or combinations thereof that may aid in comfort as well as in achieving a more custom fit for the user. The padding 306 may be formed from any suitable material, including, but not limited to, a viscoelastic foam (e.g., memory foam), an open-cell foam, a closed-cell foam, or combinations thereof.

In one embodiment, the differential limb socket 300 includes a plurality of ventilation features 310 suitable for promoting air flow through the differential limb socket 300. The ventilation features 310 may include, but are not limited to, ventilation apertures 312, ventilation channels 314, or combinations thereof. The ventilation apertures 312 may direct air into limb receptable of the cup 304 via ventilation channels 314 during use while conversely serving as drainage in the opposite direction for rain or other elements experienced during times of non-use. The ribs forming the sides of the ventilation channels 314 also aid in providing additional support strength to the differential limb socket 300.

The differential limb socket 300 may also include a moisture wicking layer 316 suitable for removing moisture from a surface of the differential limb while the differential limb is disposed within the differential limb socket 300. It some embodiments, the moisture wicking layer is in addition to any padding 306 while in other embodiments padding 306, such as open cell foam, may serve a dual purpose as both the padding 306 and a moisture wicking layer 316.

Figure 9:
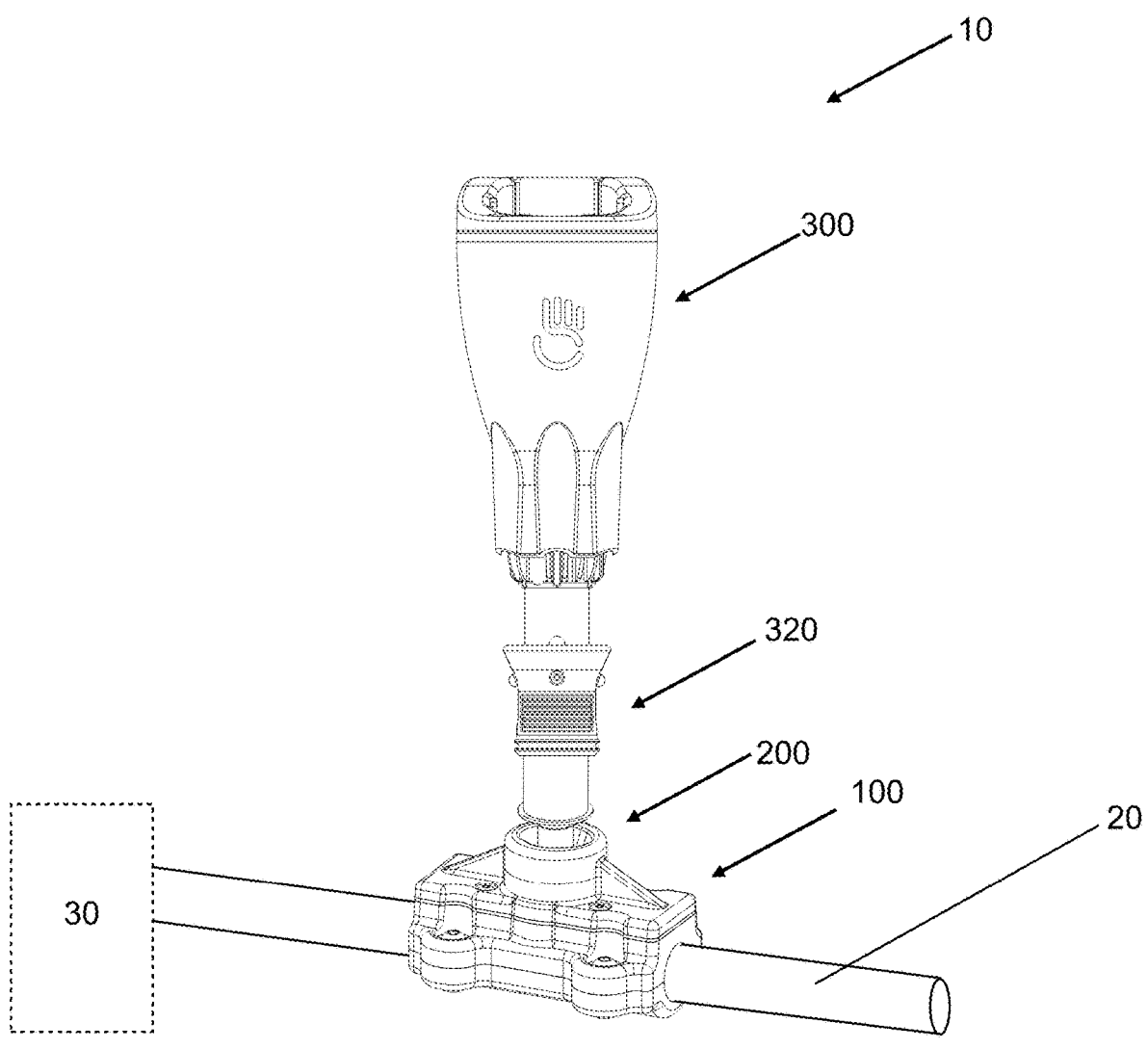
FIG. 9 is a perspective view of the limb differential handle adapter of FIG. 1 attached to a handle, according to an embodiment of the present disclosure.

Referring to FIG. 9, the handle 20 may be any suitable gripping device of any vehicle, conveyance, equipment, machinery, or apparatus 30, including, but not limited to, a simple handle, a stroller handle, a carriage handle, a cart handle, a hand truck handle, a handlebar, bicycle handlebar, a motorcycle handlebar, a moped handlebar, an ATV handlebar, a jet ski handlebar, a snowmobile handlebar, or a lever.

Referring to FIGS. 1-9, in one embodiment a limb differential handle adapter kit includes a limb differential handle adapter 10. The limb differential handle adapter includes a split coupling mount 100 configured to removably attach to a handle 20, a rotational ball-and-socket joint 208, and a differential limb socket 300. The split coupling mount 100 includes a seat portion 210 and a cap portion 212 cooperating to define a socket 202, a ball interface 204 disposed in the socket 202, and a shaft 206 extending from the ball interface 204. The differential limb socket 300 includes at least one replaceable modular insert 302 proportioned to accommodate the differential limb. The at least one replaceable modular insert 302 includes a plurality of ventilation features 310. The limb differential handle adapter 10 is free of locking mechanisms restricting disengagement of the differential limb from the differential limb socket. The differential limb socket 300 is attached to the shaft 206 of the rotational joint 200. The kit further includes a plurality of interchangeable components 304 for the at least one replaceable modular insert 302 to adjust for length, diameter, and shape of the differential limb. The kit further includes a plurality of shims 214 for disposal between the seat portion 210 and the cap portion 212 of the rotational ball-and-socket joint 208 such friction of the rotational joint 200 is adjustable by incorporation of one or more of the plurality of the shims 214 in the rotational ball-and-socket joint 208. The differential limb socket 300 is attached to the rotational joint 200 via a releasable connector 320 that is a quick-release connector disengageable without use of tools and with a single hand. The at least one replaceable modular insert 302 may further include a releasable connector 320.

Unless otherwise state, the various embodiments disclosed herein may be combined with one another in whole or in part.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A limb differential handle adapter, comprising:
a split coupling mount configured to removably attach to a handle, the split coupling mount including a lower portion having a lower curved channel disposed in an upper surface of the lower portion and an upper portion having an upper curved channel disposed in a lower surface of the upper portion such that as reversibly assembled the lower curved channel and the upper curved channel cooperate to form a coupling conduit having an internal surface configured to contact the handle around a periphery of the handle, the split coupling mount further including a plurality of fasteners spaced along an elongate dimension of the handle configured to reversibly tighten the upper portion to the lower portion;
a rotational joint configured to directly and removably attach to and extend from an upper surface of the upper portion of the split coupling mount and be free of direct attachment to the lower portion of the split coupling mount, the rotational joint including a socket, an interface disposed in the socket, and a shaft extending from the interface; and
a differential limb socket configured to receive a differential limb and including at least one replaceable modular insert proportioned to accommodate the differential limb, the differential limb socket being removably coupled to the rotation joint.

2. The limb differential handle adapter of claim 1, wherein the limb differential handle adapter is free of locking mechanisms restricting disengagement of the differential limb from the differential limb socket.

3. The limb differential handle adapter of claim 1, wherein the at least one replaceable modular insert includes a plurality of interchangeable components selected from a kit combinable to adjust for length, diameter, and shape of the differential limb.

4. The limb differential handle adapter of claim 3, wherein the plurality of interchangeable components includes padding formed from a material selected from the group consisting of a viscoelastic foam, an open-cell foam, a closed-cell foam, and combinations thereof.

5. The limb differential handle adapter of claim 1, wherein the differential limb socket includes a plurality of ventilation features selected from the group consisting of ventilation apertures, ventilation channels, and combinations thereof.

6. The limb differential handle adapter of claim 1, wherein the differential limb socket includes two socket covers which cooperate to form an exterior surface of the differential limb socket, each of the two socket covers being identical to one another.

7. The limb differential handle adapter of claim 1, wherein the rotational joint is selected from the group consisting of a ball-and-socket joint, a condyloid joint, a saddle joint, a hinge joint, a pivot joint, a plane joint, a compound joint, and combinations thereof.

8. The limb differential handle adapter of claim 1, wherein the differential limb socket is attached to the shaft of the rotational joint.

9. The limb differential handle adapter of claim 1, wherein the differential limb socket is attached to the socket of the rotational joint.

10. The limb differential handle adapter of claim 1, wherein the rotational joint includes an adjustable rotational resistance.

11. The limb differential handle adapter of claim 10, wherein the rotational joint includes a seat portion and a cap portion, and the adjustable rotational resistance is adjustable by insertion of at least one shim between the seat portion and the cap portion such that the at least one shim changes friction of the rotational joint.

12. The limb differential handle adapter of claim 1, wherein the rotational joint includes a seat portion and a cap portion, the cap portion is angled so as to limit rotation of the differential limb socket to a predetermined range of orientations, and the cap portion is attachable to the seat portion in a predetermined number of positions such that the predetermined range of orientations is adjustable rotationally relative to the seat portion.

13. The limb differential handle adapter of claim 1, wherein the rotational joint includes a seat portion and a cap portion, the cap portion being selected from a kit having different cap angles and predetermined ranges of orientations.

14. The limb differential handle adapter of claim 1, wherein the differential limb socket is attached to the rotational joint via a quick-release connector that is disengageable without use of tools and with a single hand.

15. The limb differential handle adapter of claim 1, wherein the handle is a handlebar.

16. The limb differential handle adapter of claim 15, wherein the handlebar is a bicycle handlebar.

17. The limb differential handle adapter of claim 15, wherein the handlebar is a motorcycle handlebar, a moped handlebar, an all-terrain vehicle handlebar, a jet ski handlebar, or a snowmobile handlebar.

18. The limb differential handle adapter of claim 1, wherein the handle is a stroller, carriage, cart, or hand truck handle.

19. The limb differential handle adapter of claim 1, wherein the lower portion of the split coupling mount is a first body and the upper portion of the split coupling mount is a second body, the first body being non-monolithic with the second body.

20. The limb differential handle adapter of claim 1, wherein the shaft is cylindrical.

21. A limb differential handle adapter kit, comprising:
  a limb differential handle adapter, including:
    a split coupling mount configured to removably attach to a handle, the split coupling mount including a lower portion having a lower curved channel disposed in an upper surface of the lower portion and an upper portion having an upper curved channel disposed in a lower surface of the upper portion such that as reversibly assembled the lower curved channel and the upper curved channel cooperate to form a coupling conduit having an internal surface configured to contact the handle around a periphery of the handle, the split coupling mount further including a plurality of fasteners spaced along an elongate dimension of the handle configured to reversibly tighten the upper portion to the lower portion;
    a rotational ball-and-socket joint configured to directly and removably attach to and extend from an upper surface of the upper portion of the split coupling mount and be free of direct attachment to the lower portion of the split coupling mount, the rotational joint including a seat portion and a cap portion cooperating to define a socket, a ball interface disposed in the socket, and a shaft extending from the ball interface; and
    a differential limb socket configured to receive a differential limb and including at least one replaceable modular insert proportioned to accommodate the differential limb, the at least one replaceable modular insert including a plurality of ventilation features selected from the group consisting of ventilation apertures, ventilation channels, and combinations thereof,
  wherein:
    the limb differential handle adapter is free of locking mechanisms restricting disengagement of the differential limb from the differential limb socket;
    the differential limb socket is attached to the shaft of the rotational joint;
    the kit further includes a plurality of interchangeable components for the at least one replaceable modular insert to adjust for length, diameter, and shape of the differential limb;
    the kit further includes a plurality of shims for disposal between the seat portion and the cap portion of the rotational ball-and-socket joint such friction of the rotational joint is adjustable by incorporation of one or more of the plurality of the shims in the rotational ball-and-socket joint; and
    the differential limb socket is attached to the rotational joint via a quick-release connector that is disengageable without use of tools and with a single hand.

22. The limb differential handle adapter kit of claim 21, wherein the handle is a bicycle handlebar.

* * * * *